(12) United States Patent
Rocheleau et al.

(10) Patent No.: US 11,680,831 B2
(45) Date of Patent: Jun. 20, 2023

(54) LASER LOWERING DEVICE

(71) Applicant: SheaRock Construction Group Inc., Windsor (CA)

(72) Inventors: Daryl Rocheleau, Windsor (CA); Michael Allen Snowdon, Tecumseh (CA)

(73) Assignee: SheaRock Construction Group Inc., Windsor (CA)

( * ) Notice: Subject to any disclaimer, the term of this patent is extended or adjusted under 35 U.S.C. 154(b) by 0 days.

(21) Appl. No.: 17/339,920

(22) Filed: Jun. 4, 2021

(65) Prior Publication Data

US 2021/0389164 A1 Dec. 16, 2021

(51) Int. Cl.
| | |
|---|---|
| *G01D 11/30* | (2006.01) |
| *F16C 1/10* | (2006.01) |
| *F16M 11/06* | (2006.01) |
| *G06T 7/13* | (2017.01) |
| *G06T 7/149* | (2017.01) |
| *G16H 50/20* | (2018.01) |

(52) U.S. Cl.
CPC ............... *G01D 11/30* (2013.01); *F16C 1/10* (2013.01); *F16M 11/06* (2013.01); *G06T 7/13* (2017.01); *G06T 7/149* (2017.01); *G16H 50/20* (2018.01); *G06T 2207/20182* (2013.01); *G06T 2207/30016* (2013.01)

(58) Field of Classification Search
CPC .......... G01D 11/30; F16C 1/10; F16C 11/045; F16C 7/00; F16M 11/06; F16M 11/10; F16M 13/00; G06T 7/13; G06T 7/149; G06T 2207/20182; G06T 2207/30016; G16H 50/20
USPC ....................................................... 248/514
See application file for complete search history.

(56) References Cited

U.S. PATENT DOCUMENTS

| | | | |
|---|---|---|---|
| 2016/0303743 A1* | 10/2016 | Rockrohr | A61B 17/00234 |
| 2017/0007344 A1* | 1/2017 | Seow | F16H 19/08 |
| 2018/0001832 A1* | 1/2018 | Nickel | B60N 2/2827 |
| 2019/0242728 A1* | 8/2019 | Low | B25J 15/0019 |
| 2020/0315722 A1* | 10/2020 | Penny | A61B 90/08 |
| 2020/0375680 A1* | 12/2020 | Penny | A61B 34/37 |

\* cited by examiner

*Primary Examiner* — Muhammad Ijaz
(74) *Attorney, Agent, or Firm* — David J. Schnurr

(57) ABSTRACT

A laser lowering device for mounting a laser, which in one embodiment includes: at least one laser support for mounting the laser; a mount having a line receiving portion, the mount being connected to the at least one laser support; an elongated member having a first end and a second end, the first end being removably connected to a pole and the second end being pivotally connected to the mount; and a mount control line connected to the line receiving portion and extending towards the elongated member. The mount control line is manipulable to cause the mount to pivot relative to the elongated member. The laser lowering device allows a laser to be remotely lowered into a non-traditional manhole and inserted into pipes.

12 Claims, 16 Drawing Sheets

LASER LOWERING DEVICE

TECHNICAL FIELD

The disclosure relates generally to pipe laser equipment.

BACKGROUND

Sewer pipes are installed as part of an underground pipe system and used to carry sewage and clean water from one location to another. These sewers are designed and very specific to grades and alignments provided from engineered drawings. Contractors are required to install these sewers to very strict tolerances as designed. At the installation stage, pipe lasers are used to maintain contact grade and alignment from one manhole to the next. Pipe lasers are commonly used in conjunction with sewer installations around the world.

Manholes provide access to the sewer for maintenance purposes. Manholes are considered a confined space according to occupational health and safety guidelines. Over the course of the last few decades, manufacturers have developed the tools to eliminate the need for human entry into a sewer, thereby reducing the size requirements for traditional manholes. In many parts of the world, the pipe laser is an integral part of the sewer installation, and in a common installation method, trenches are left open between manholes and the laser is disposed on top of a sewer pipe rather than inside. In contrast, in many North America installations, sewers are installed with the pipe laser inside the pipe.

Where the laser is disposed inside the pipe, a worker needs access into the manhole to set it up. For a worker to gain access into the sewer, a long list of conditions must be met before access will be allowed under law (e.g. training, confined space entry permit, testing of air quality, introducing clean air, developing a rescue plan, setting up tripod, harness for the entrant, etc.). This in turn requires a significant amount of time and cost to the contractor and safety concerns for the worker. The dangers to the worker accessing the sewer include lack of oxygen, toxic gases including carbon monoxide and hydrogen sulfide (H2S), among other dangers. With the advent of non-traditional sewer installations, which are not sized to permit human access, surface installation (i.e. without having a worker access the sewer) is necessary.

SUMMARY

The present disclosure provides a laser lowering device that is capable of mounting and lowering various models of pipe lasers down narrower, non-traditional manholes. The device of the present disclosure can be attached to various types and models of poles and allows for remote placement, from the surface, of a pipe laser into an outlet pipe. The device can also be easily be adapted to work with various models of pipe lasers. The device can pivot a mounted pipe laser 180 degrees longitudinally, which will allow for the placement of pipe lasers in varying orientations of outlet pipes. For example, the laser lowering device can be lowered in an angled orientation that will allow a mounted pipe laser to be easily placed in a downward sloping outlet pipe. The specific design of the device allows for easy rotation along its longitudinal plane. The device is dimensioned and formed of materials to enable it to work in narrower, non-traditional riser shafts and still withstand the harsh, corrosive environments of underground piping systems.

In one aspect, the disclosure describes a laser lowering device for mounting a laser, which includes: at least one laser support for mounting the laser; a mount having a line receiving portion, the mount being connected to the at least one laser support; an elongated member having a first end and a second end, the first end being removably connected to a pole and the second end being pivotally connected to the mount; and a mount control line connected to the line receiving portion and extending towards the elongated member. The mount control line is manipulable to cause the mount to pivot relative to the elongated member.

In some embodiments, the mount is in a shape that provides for the line receiving portion to be in an offset position from a center axis of the elongated member.

In some embodiments, the mount is in the shape of a triangle.

In some embodiments, the elongated member includes a protruded portion in between the first end and the second end.

In some embodiments, the elongated member further includes a rod disposed of in the protruded portion.

In some embodiments, the laser lowering further includes a first sheave at the line receiving portion and a second sheave disposed of on the rod.

In some embodiments, the mount control line is configured to wrap around at least a portion of each of the first sheave and the second sheave and is operable to cause the mount to pivot when manipulated.

In some embodiments, the elongated member further includes an aperture disposed of near the protruded portion.

In some embodiments, the mount control line is configured to wrap around at least a portion of each of the first sheave and the second sheave, extends through the aperture and is operable to cause the mount to pivot when manipulated.

In some embodiments, the at least one laser support comprises an upper support member and a lower support member.

In some embodiments, the lower support member is angled inwards relative to the mount.

In some embodiments, wherein the lower support comprises a plurality of holes for mounting the laser.

Further details of these and other aspects of the subject matter of this application will be apparent from the detailed description included below and the drawings.

DESCRIPTION OF THE DRAWINGS

Reference is now made to the accompanying drawings, in which.

DETAILED DESCRIPTION OF EXAMPLE EMBODIMENTS

Figure 1:
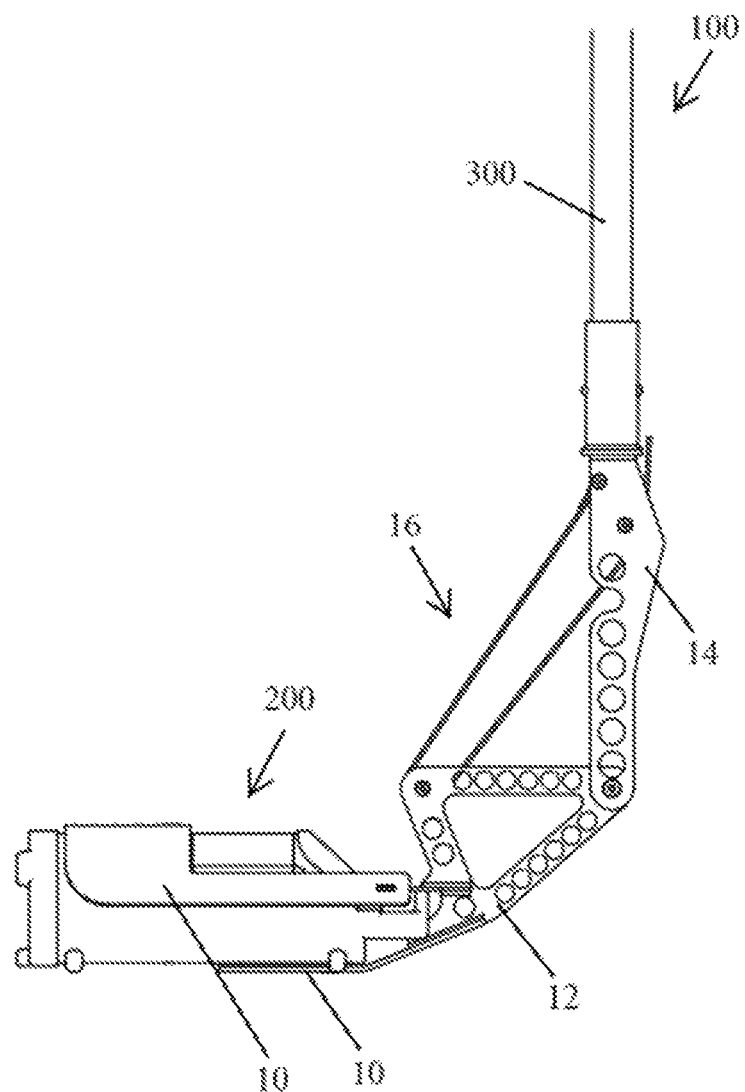
FIG. 1 is a side view of an embodiment of a laser lowering device, with a connected pole, shown with a mounted laser in a retracted position.
Figure 2:
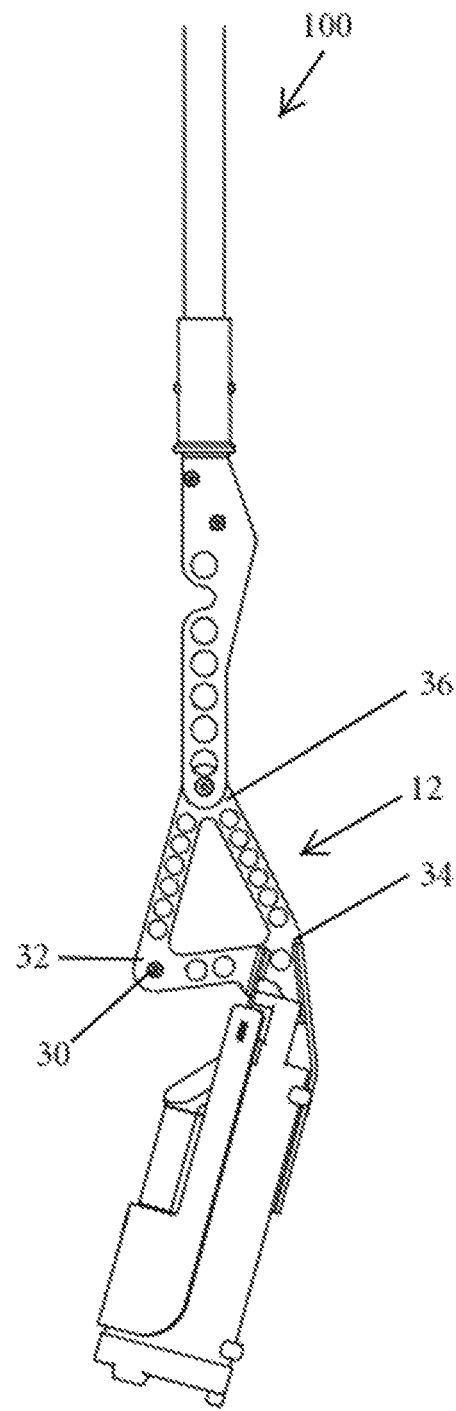
FIG. 2 is a side view of the embodiment of the laser lowering device of FIG. 1, shown with a mounted laser in an expanded position.
Figure 3:
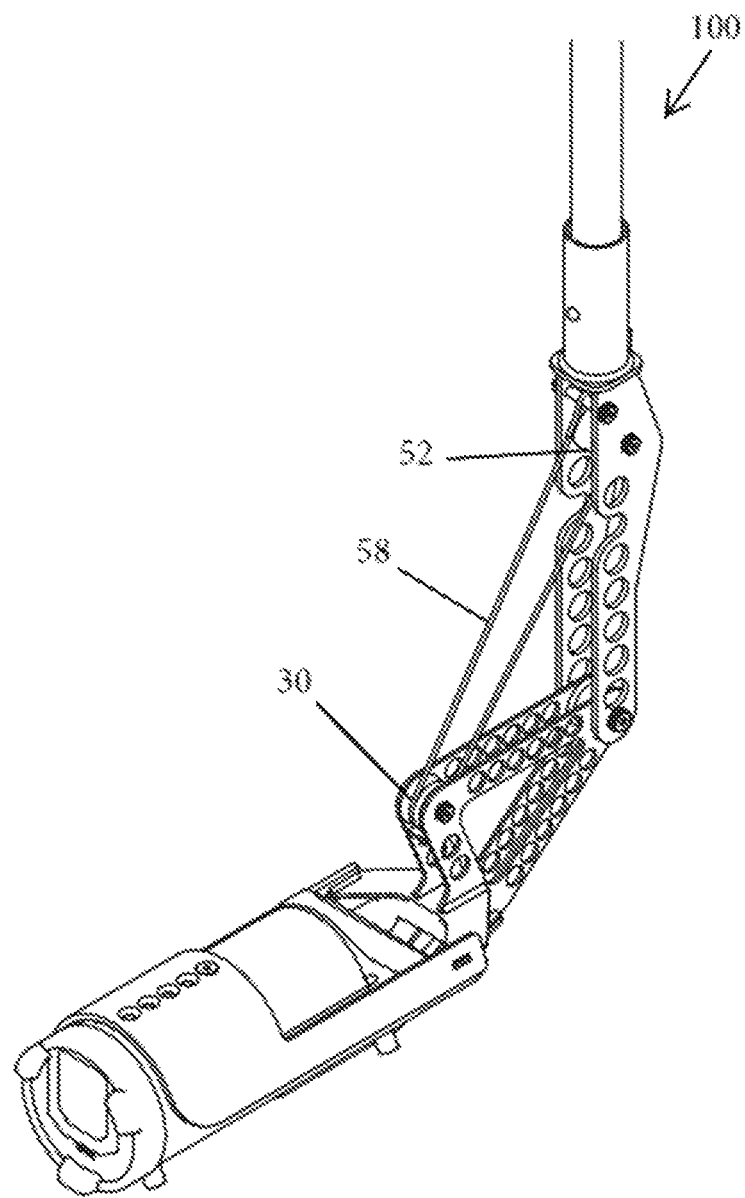
FIG. 3 is a perspective front view of the embodiment of the laser lowering device of FIG. 1, shown with a mounted laser in a retracted position.
Figure 4:
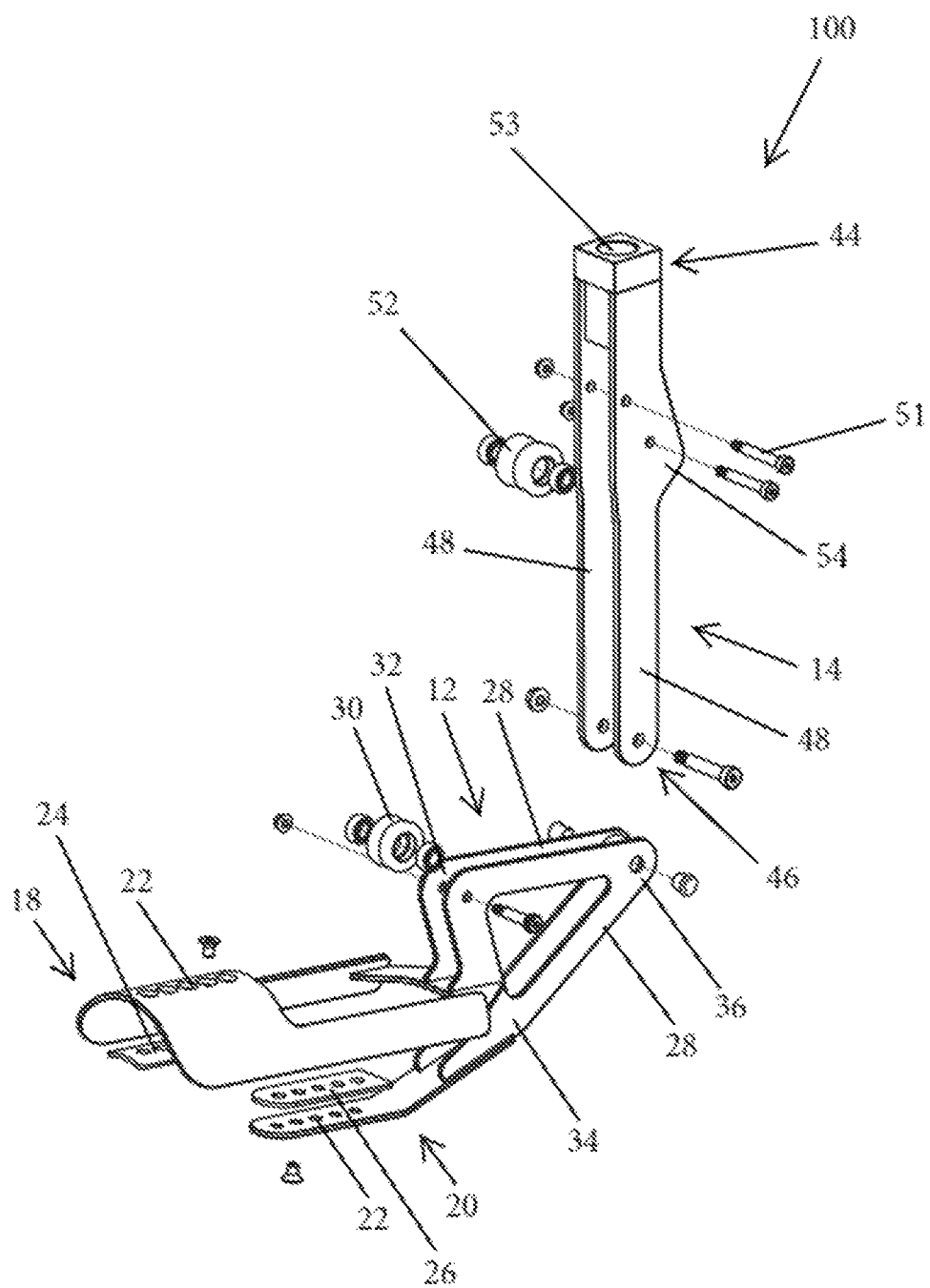
FIG. 4 is an exploded perspective front view of another embodiment of a laser lowering device.
Figure 5:
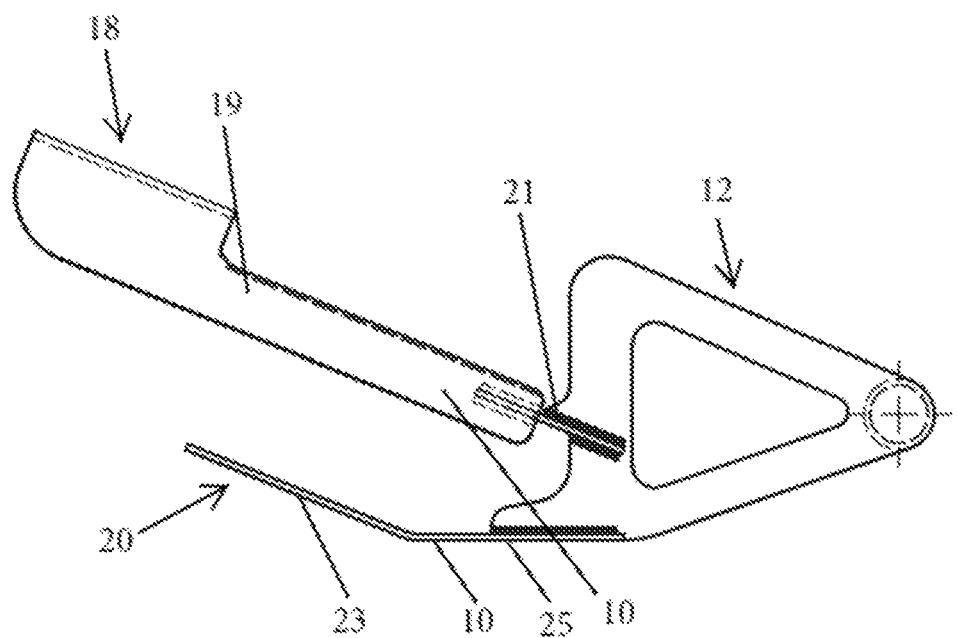
FIG. 5 is a side view of the pair of supports and the triangular mount of the embodiment of the laser lowering device of FIG. 4.
Figure 6:
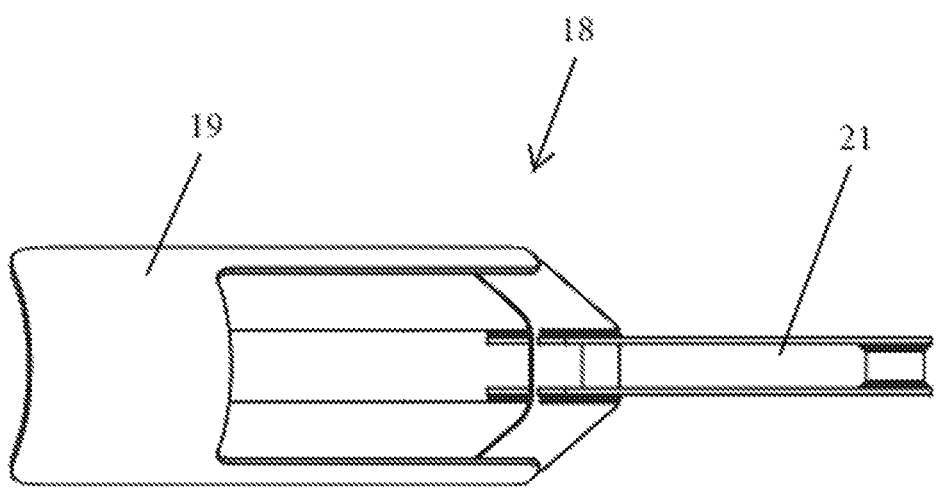
FIG. 6 is a top view of upper support member of the embodiment of the laser lowering device of FIG. 4.
Figure 7:
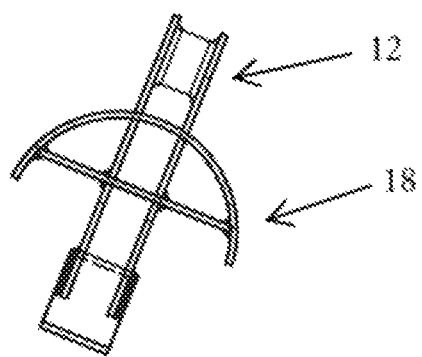
FIG. 7 is a front view of the pair of supports and the triangular mount of the embodiment of the laser lowering device of FIG. 4.
Figure 8:
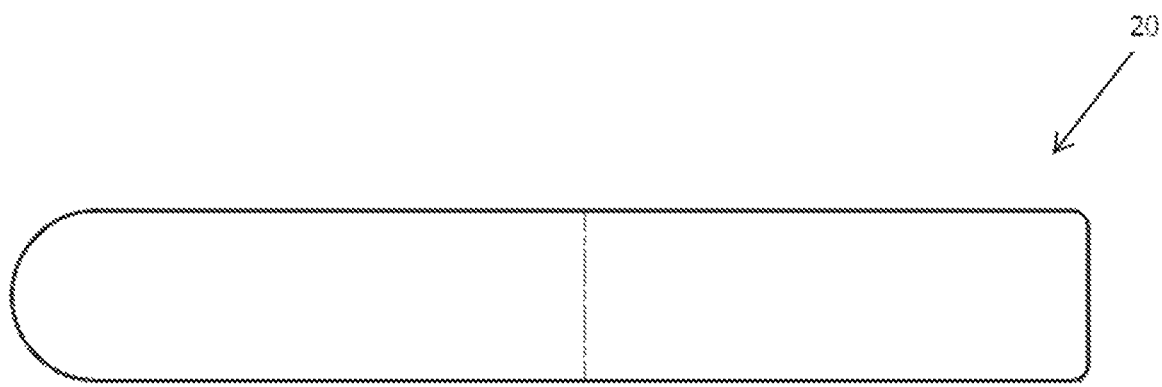
FIG. 8 is a top view of the lower support member of the embodiment of the laser lowering device of FIG. 4.
Figure 9:
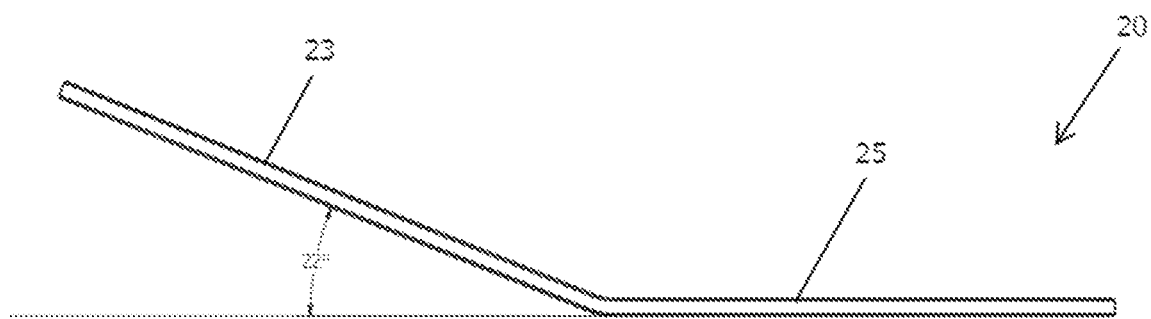
FIG. 9 is a side view of the lower support member of the embodiment of the laser lowering device of FIG. 4
Figure 10:
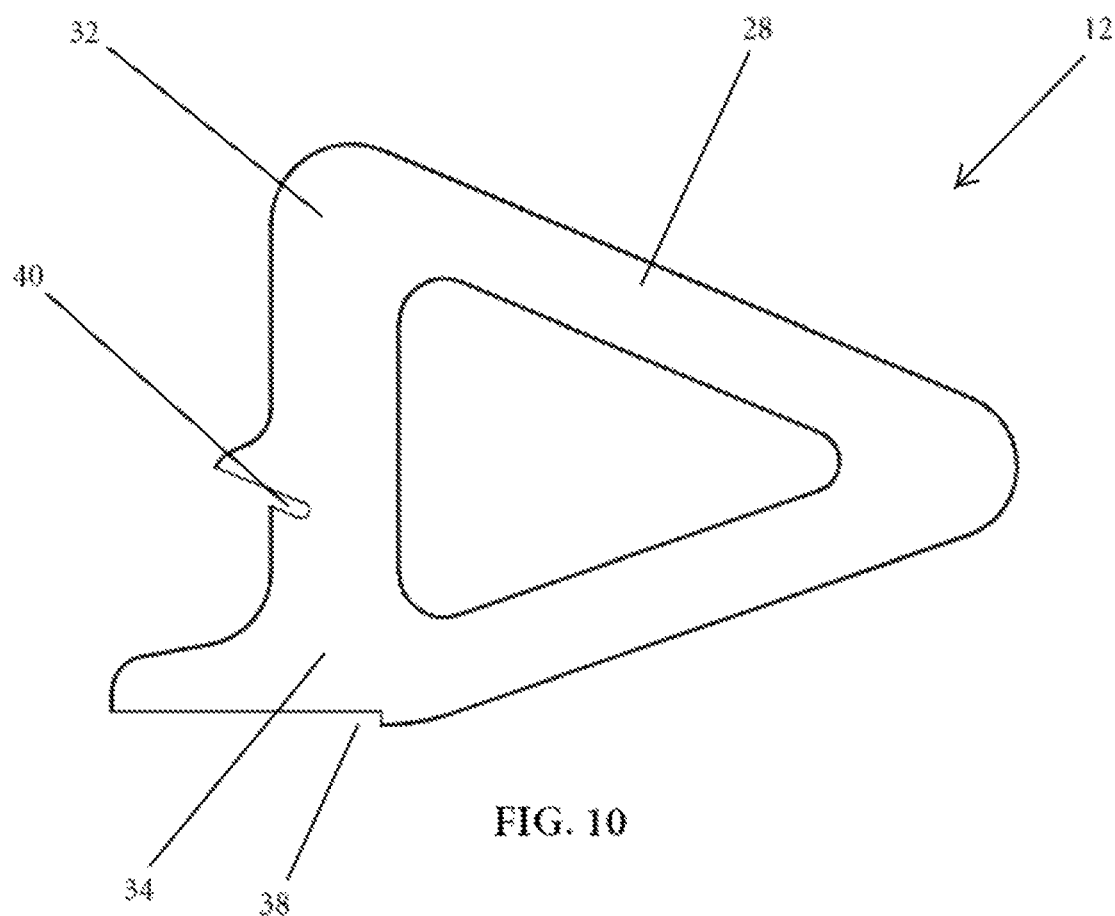
FIG. 10 is a side view of the triangular mount of the embodiment of the laser lowering device of FIG. 4.
Figure 11:
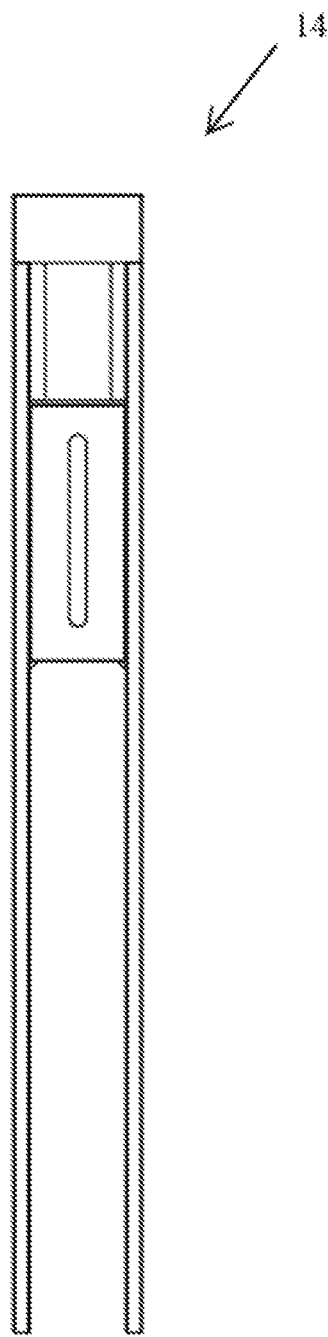
FIG. 11 is a back view of the elongated member of the embodiment of the laser lowering device of FIG. 4.
Figure 12:
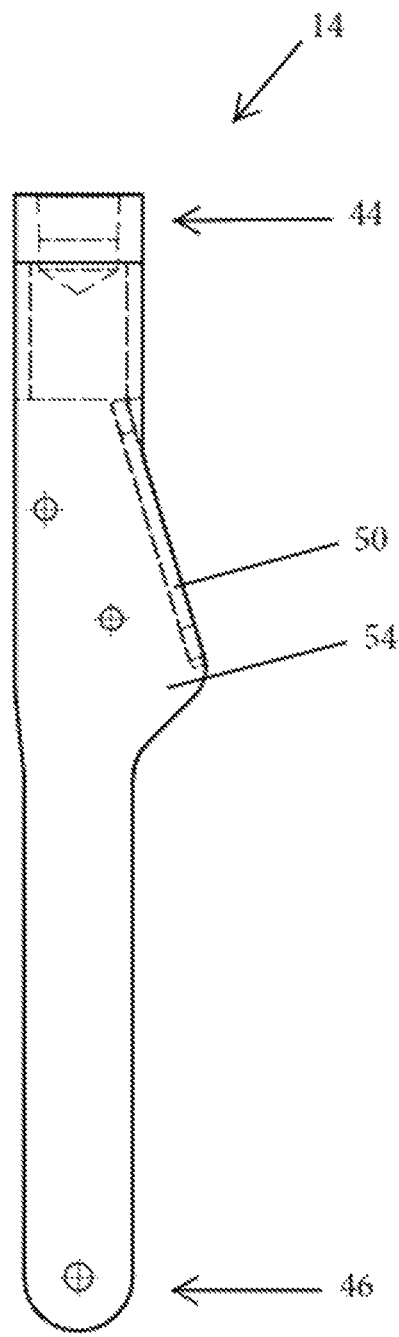
FIG. 12 is a left side view of the elongated member of the embodiment of the laser lowering device of FIG. 4.
Figure 13:
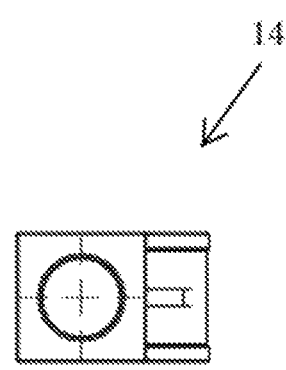
FIG. 13 is a top view of the elongated member of the embodiment of the laser lowering device of FIG. 4.
Figure 14:
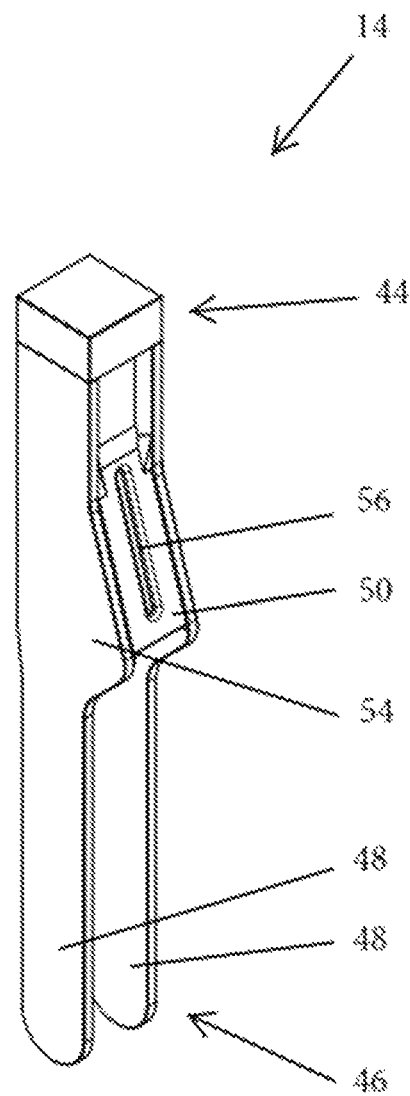
FIG. 14 is a perspective back view of the elongated member of the embodiment of the laser lowering device of FIG. 4.
Figure 15:
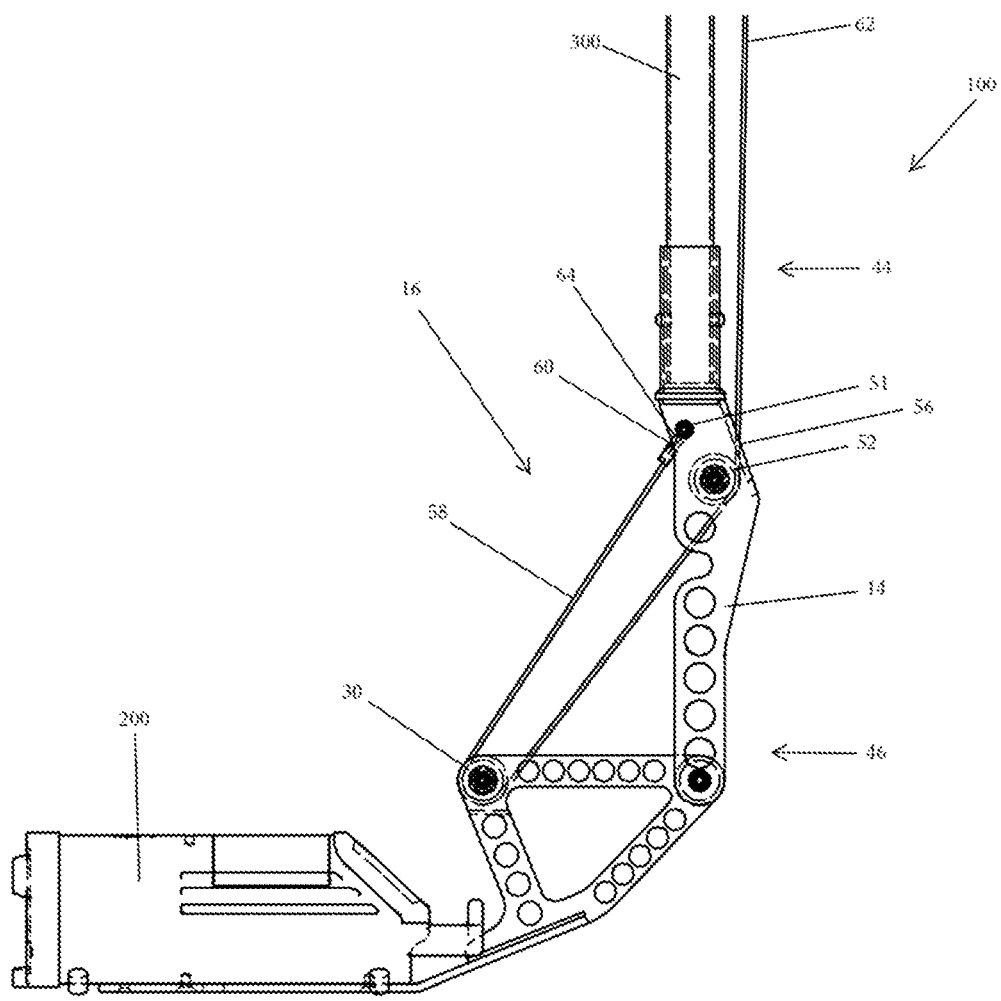
FIG. 15 is a cross-section side view of another embodiment of a laser lowering device, with a connected pole, and shown with a mounted laser.
Figure 16:
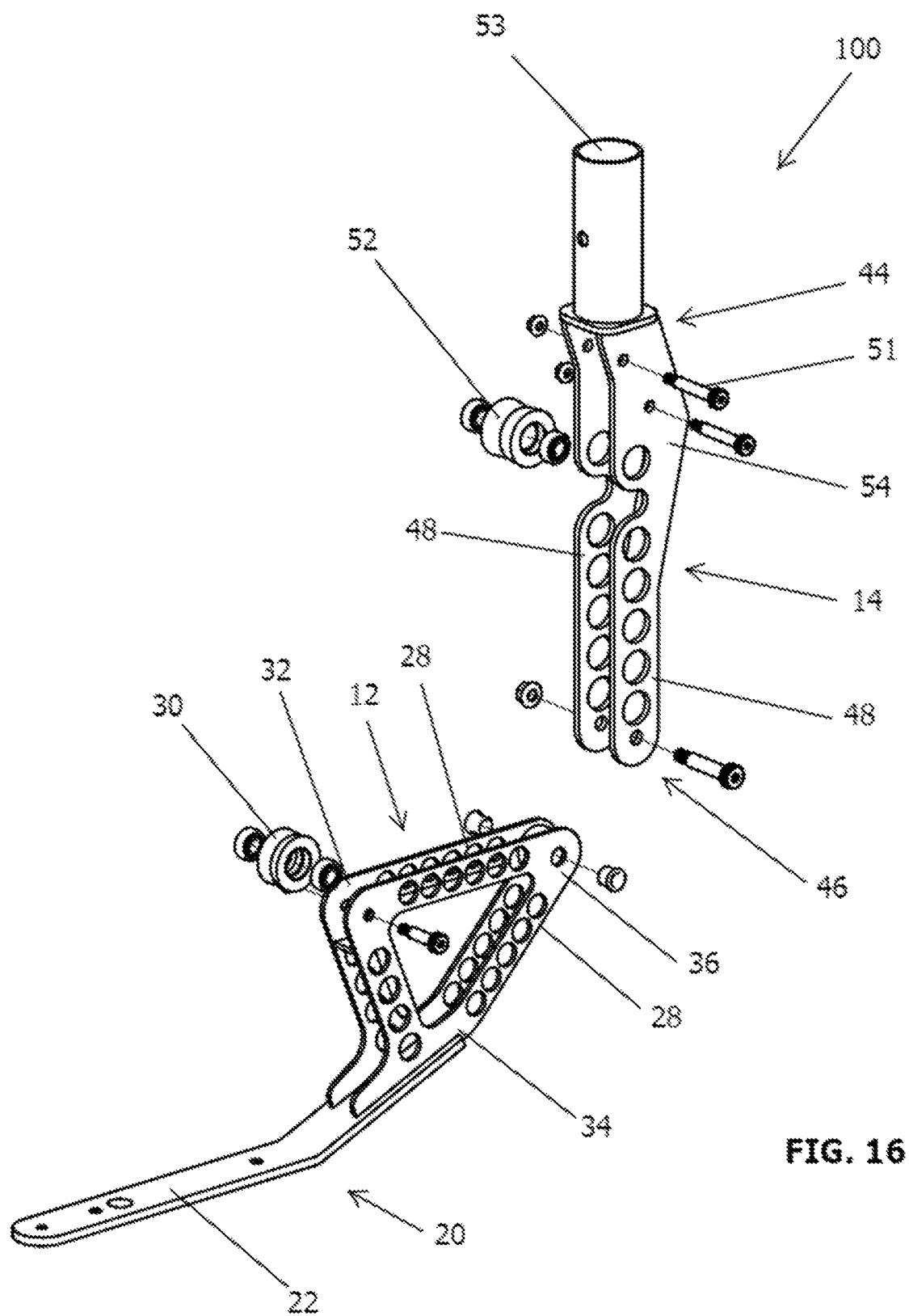
FIG. 16 is an exploded perspective front view of the embodiment of a laser lowering device of FIG. 15.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. In particular, all terms used herein are used in accordance with their ordinary meanings unless the context or definition clearly indicates otherwise. Also, unless indicated otherwise except within the claims the use of "or" includes "and" and vice-versa. Non-limiting terms are not to be construed as limiting unless expressly stated or the context clearly indicates otherwise (for example, "including", "having", "characterized by" and "comprising" typically indicate "including without limitation"). Singular forms included in the claims such as "a", "an" and "the" include the plural reference unless expressly stated or the context clearly indicates otherwise. Further, the stated features and/or configurations or embodiments thereof the suggested intent may be applied as seen fit to certain operating conditions or environments by one experienced in the field of art.

By way of background, the process of designing the device of the present invention started with fully understanding the constraints and functionalities that would dictate the product design. The strict requirements must be considered during the early stages of the design process, and include the physical dimensions of the riser shaft and pit body, as well as the underlying functionality of the device being to place a pipe laser horizontally in a pipe from the surface. The riser shaft of non-traditional manholes are approximately 12 inches in diameter and the body of the pit itself is a 2 ft diameter sphere. Since the length of the pipe laser is longer than the diameter of the riser shaft, the laser needs to be able to rotate with the laser lowering device assembly to fit within the riser shaft. To enable pipe laser to rotate within the spherical body of the non-traditional manhole, the assembly is required to have a pivot point that could be controlled from the surface, and secondly, to have a system to allow the amount of rotation required. Keeping operational convenience in consideration, it was determined that it would be optimal for the pipe laser be able to dangle off the end of the pole from the laser lowering device's pivot point and then rotate upwards to the desired horizontal position. When pipe laser is dangling straight down by the force of gravity, the laser and the laser lowering device are in line with the length of the pole. To move from the in-line dangling position to the horizontal rotated position, a novel pulley system is employed that can be operated from the surface using a standard rope or equivalent.

Aspects of various embodiments are now described in relation to the figures.

Referring to the figures, in the embodiments shown, there is shown a laser lowering device 100 with a mounted pipe laser 200. Laser lowering device 100 includes a laser support 10, a mount 12, an elongated member 14, and a pulley system 16. Laser support 10 is connected to mount 12. Mount 12 is connected to elongated member 14. Pulley system 16 extends from elongated member 14 to mount 12 and back to elongated member 14.

Referring to the figures, laser support 10 includes a lower support member 20, and may alternatively include an upper support member 18. In the embodiments shown, upper support member 18 includes an upper laser support portion 19 and an upper support member connector portion 21. Lower support member 20 includes a lower laser support portion 23 and a lower support member connector portion 25. Lower support member 20 supports a mounted pipe laser 200 on the device 100, wherein the pipe laser 200 is adapted to be secured to the lower support member 20 (for example, using a male/female connection, or other connection configuration). In an alternative embodiment, both upper support member 18 and lower support member 20 support a mounted pipe laser 200. As illustrated in the figures, pipe lasers 200 are designed to be placed in round outlet pipes, so each brand of pipe laser 200 has a generally cylindrical-type body geometry with minor differences across each brand. Accordingly, in one embodiment, upper laser support portion 19 has a curved surface that conforms to the curvature of the top of pipe laser 200 to prevent horizontal rotation. Lower laser support portion 23 has a flat surface and does not offer any lateral support. However, during the design process, it has been found that lower support member 20 on its own provides sufficient support for pipe laser 200. In some embodiments, upper support member 18 and lower support member 20 hold pipe laser 200 to laser lowering device 100 from both the top and bottom, respectively. As illustrated in the figures, both upper support member 18 and lower support member 20 have a plurality of non-threaded through holes 22. The plurality of non-threaded through holes 22 are configured to correspond with the threaded mounting holes common to many pipe lasers 200. Across all of the brands of pipe lasers 200, each has a threaded mounting hole in a different location for the pipe laser 200 to be fastened to a stand or other attachments. The plurality of non-threaded through holes 22 utilize these threaded mounting holes on pipe lasers 200 as a way for the pipe lasers 200 to be fastened to laser support 10 and laser lowering device 100. The variation in the locations of threaded mounting holes across the different brands of pipe lasers 200 is accommodated for in the location of corresponding non-threaded through holes 22 on both upper support member 18 and lower support member 20 as well as in the precise shape and size of upper support member 18 and lower support member 20. Optionally, upper support member 18 may include an upper rubber pad 24 and lower support member 20 may include a lower rubber pad 26. Upper rubber pad 24 is placed in between upper support member 18 and pipe laser 200. Lower rubber pad 26 is placed in between lower support member 20 and pipe laser 200.

Referring to the figures, in the embodiments shown, laser support 10 is connected to mount 12. Mount 12 includes two parallel frames 28, and a freely rotating first sheave (or pulley) 30. The freely rotating first sheave (or pulley) is an example of a line receiving portion. As illustrated, mount 12 is generally in the shape of a triangle, however, a person skilled in the art would understand that mount 12 could be in a variety of suitable geometric shapes. A triangular shape is chosen for the strength and stability it can provide. In the figures, frames 28 are in the shape of an isosceles triangle with a first base vertex 32, a second base vertex 34 and an apex 36. First sheave 30 is interposed between frames 28 at first base vertex 32. Lower support member 20 is welded (or otherwise fixedly secured) to frames 28 at or about second base vertex 34. In an alternate embodiment, upper support member 18 is also welded (or otherwise fixedly secured) to frames 28. Frames 28 further include a first cutout 38 on the outer edge of the second base vertex 34. In an alternative embodiment, frames 28 also include a second cutout 40 interposed between first base vertex 32 and second base vertex 34. Lower support member 20 is welded (or otherwise fixedly secured) to mount 12 at first cutout 38, and in an alternative embodiment, upper support member 18 is welded to mount 12 at second cutout 40.

Referring to the figures, lower support member 20 is orientated at an angle 42 with respect to mount 12. Angle 42 is the angle by which lower support member 20 is bent inward relative to the mount 12. In one particular embodiment, and as illustrated in the figures, angle 42 is approximately 22 degrees. In other embodiments, angle 42 may be higher or lower than 22 degrees. The inward angle configuration of the lower support member 20 relative to the mount 12 functions to prevent pipe laser 200 from hanging directly in-line with (or directly in the same vertical plane as) elongated member 14 when the device 100 is being lowered into a pipe, which in turn reduces the amount of force or effort required by the user to draw mount 12 upward into its operating position, and ultimately assists in the rotation of pipe laser 200 into the pipes. Angling the lower support member 20 inward relative to the mount 12 also serves to reduce the amount of distance a user must pull on mount control line 58 to rotate pipe laser 200 into the correct position. Another benefit of the angled orientation of lower support member 20 is that it allows pipe laser 200 to be lowered down the riser shaft with mount 12 pivoted to a position where mount 12 is folded up into elongated member 14. A further benefit of angling the lower support member 20 relative to the mount 12 is that this configuration enables the legs of pipe laser 200 to make contact with the pipe floor (without any interference by the lower support member 20) when the pipe laser 200 is positioned horizontally (see FIG. 1 configuration) within the pipe. The legs of pipe laser 200 must make contact with the pipe floor (and no part of the device 100 should make contact with the pipe floor), in order for the pipe laser 200 to function properly. In this regard, many pipe lasers are programmed not to function unless or until the pipe laser feet are balanced and level, and in contact with the pipe floor.

Referring the figures, in the embodiments shown, the shape and size of upper support member 18 and lower support member 20 are designed to be easily modified to adjust to different brands and models of pipe lasers 200, as well as to maintain strength and stability to support the weight of pipe laser 200 and to not interfere with the proper functioning of pipe laser 200. Ease of modification is achieved by the division of upper support member 18 and lower support member 20 into its constituent portions. For example, upper support member 18 has upper laser support portion 19, which can be modified according to the size and shape of pipe laser 200, while maintaining the same attachment mechanism to mount 12 with a standardized upper support member connector portion 21. Ease of modification is desired due to the existence of multiple brands of pipe lasers 200 on the market with each one having a different shape and weight. Laser lowering device 100 is designed to be used around the world, including all over North America, and will be purchased by users who use different brands of pipe lasers 200. Accordingly, it is very important that the laser lowering device can accommodate and be used with each type of pipe laser 200. Regardless of the size and shape of upper support member 18 and lower support member 20, they are designed to be secured to mount 12 in the same manner through the use of the standardized upper support member connector portion 21, lower support member connector portion 25, and optional first and second cutouts 38, 40.

Referring to the figures, in the embodiments shown, mount 12 is pivotally connected to elongated member 14. Elongated member 14 is an elongated member with a first end 44 opposite a second end 46. Elongated member 14 may be a unitary construction. Alternatively, in the embodiments shown, elongated member 14 includes two parallel elongated plates 48, a slotted plate 50, a second sheave 52, a bolt 51, and a pole receiving cavity 53 configured as described below. Elongated plates 48 include a protruded portion 54 between first end 44 and second end 46. Slotted plate 50 is interposed between elongated plates 48 at protruded portion 54. Slotted plate 50 is a square plate with an elongated slot cutout or aperture 56 at its center. The elongated slot cutout 56 is shaped to keep the mount control line 58 aligned with the second sheave 52. Second sheave 52 is a freely rotating sheave interposed between elongated plates 48 at protruded portion 54. Second sheave 52 is interposed between elongated plates 48 at protruded portion 54 to allow second sheave 52 to be placed in a position offset from the center axis of elongated member 14, and ultimately offset from the center axis of pole 300. The offset position of the second sheave and elongated slot cutout 56 assists with keeping mount control line 58 running roughly parallel with elongated member 14 and pole 300, which in turn helps to reduce friction and the resulting wear and tear on mount control line (or rope) 58, which friction (and increased wear and tear) would result if the mount control line 58 were disposed in a non-offset (or parallel) configuration relative to pole 300 when the mount control line 58 is moved relative to second sheave 52. For example, if the mount control line 58 is moved vertically, the mount control line would rub against pole 300 if not for the off-set position of second sheave 52. In the example embodiment shown in the drawings, bolt 51 is interposed between elongated plates 48 between first end 44 and second sheave 52. As described herein, bolts can be substituted with other securement means (for example, nut and bolt connections, screw connections, gluing, hook and loop fasteners, etc.) without impacting invention function. Second end 46 of elongated member 14 is pivotally connected to apex 36 of mount 12. Pole receiving cavity 53 is located at first end 44. In one embodiment, elongated member 14 includes a sheave cutout 57 that is dimensioned to accommodate the bolt ends used to secure first sheave 30 when mount 12 is folded up towards elongated member 14.

Referring to the figures, in one embodiment, the pulley system 16 includes first sheave 30, second sheave 52, and a mount control line 58. Mount control line 58 includes a first line end 60 and a second line end 62. First line end 60 is a closed loop 64. Closed loop 64 is secured to bolt 51, but could be secured to elongated member 14 by other conventional means. Mount control line 58 extends from bolt 51 to and around a portion of first sheave 30. From first sheave 30, mount control line 58 extends to and around a portion of second sheave 52. From second sheave 52, mount control line 58 then extends through slot cutout 56 towards first end 44 and beyond to the user.

The design process of pulley system 16 was extensive and meticulous because the locations of first sheave 30 and second sheave 52, with respect to each other, play a large role in the effort needed to operate laser lowering device 100. For example, when laser lowering device 100 and pipe laser 200 are in-line with elongated member 14, first sheave 30 and second sheave 52 cannot be in vertical alignment with each other because in order to initiate rotation of pipe laser 200, a force needs to be applied that is not in the linear direction of elongated member 14. As illustrated in the figures and the drawings generally, this was achieved through design of the pivoting portion in laser lowering device 100. In the embodiments shown, the pivoting portion is mount 12, which is an isosceles triangle in shape. Mounts of other shapes can be utilized without impacting inventive function. Apex 36 serves as the point of pivot for the laser lowering device 100. First sheave 30 is located at first base vertex 32 and laser support 10, holding pipe laser 200, is located at second base vertex 34. The offset distance of first sheave 30 from the center of the triangle, in the plane where the pivot point is located, allows the laser lowering device 100 to initiate rotation from its hanging (i.e. resting) position, where first sheave 30 is the point at which the force exerted by the user through mount control line 58 is activated. By offsetting the central pivot point which connects the elongated member 14 to the mount 12 (i.e. at the apex 36 of mount 12) from the first sheave 30, such that the first sheave 30 is positioned on the opposite side of the apex 36 from the pipe laser 200, the device 100 achieves proper balance and minimizes the profile of the device 100 and attached pipe laser 200, in order to allow the device 100 and attached pipe laser 200 to fit within the pipe.

In operation, the laser lowering device 100 has three general orientations: a folded up position; a horizontal position; and a hanging (or resting) position. The device can also be adapted for movement of the mounted pipe laser 200 to other positions by rotation about the apex 36. The folded up position is where mount 12 is folded up and partially into elongated member 14. A mounted pipe laser 200 would be parallel to, and be pointing towards first end 44 of elongated member 14 in the folded up position. The horizontal position is where the center line of mount 12, and a mounted pipe laser 200, is roughly perpendicular to elongated member 14. The hanging (or resting) position is where the center line of mount 12 is roughly in line with elongated member 14, and a mounted pipe laser 200 is pointing away from first end 44 of elongated member 12, roughly opposite to the folded up position. Laser lowering device 100 would generally be lowered down a riser shaft in either the folded up position or the dangling position. Being able to lower pipe laser 200 down a riser shaft in two different orientations gives the user more freedom and allows for pipe laser 200 to be inserted into any grade and location of pipe inlet.

The user is required to exert a forward pushing motion on to laser lowering device 100, while it is in the horizontal position, in order to insert pipe laser 200 into a pipe. The requirement for forward movement in the rotated position dictates that laser lowering device 100 cannot be lowered in using a rope and instead requires the use of a rigid apparatus, such as a pole, that the user could push against from the surface to enact that forward motion. The depth of some vertical riser shafts extends up to 7.5 meters, or 26.606 feet, and at that depth there is only 2.3 degrees of rotation available for a pole to rotate within the vertical riser shaft. Having only 2.3 degrees of available rotation means that the pole to be used with laser lowering device 100 needs to be rigid enough that it would not bend when the user attempts to insert pipe laser 200 into the pipe. As illustrated in the figures, first end 44 of laser lowering device 100 is configured to be removably attached to a pole 300, such as Cherne™ Remo™ pole. In one optional embodiment, one end of the pole 300 tapers and has a metal spring clip (not shown) that easily secures first end 44 of laser lowering device 100 to the end of the pole 300. If necessary, multiple poles 300 can be adapted to be connected end-to-end in sequence using the same spring clip so that laser lowering device 100 can be used at the maximum operating depths of vertical riser shafts.

As illustrated in the figures, laser lowering device 100 is optionally constructed from 6061 aluminum, which has a high tensile yield strength of 40,000 psi while remaining lightweight. The overall structure of laser lowering device 100 is optionally cut out of a 6061 aluminum plate. Mount 12 is optionally cut out of a 0.125 inch thick plate. Elongated member 12 and laser support 10 are optionally cut out of a 0.188 inch thick plate. Alternatively, mount 12 may be made from a thinner plate to reduce the overall weight of laser lowering device because the triangular geometry of mount 12 maintains an appropriate amount of strength with the thinner material. Unlike mount 12, elongated member 14 and laser support 10 may not have the same level of geometric strength as mount 12, so as to maintain an appropriate level of strength elongated member 14 and laser support 10 may be fabricated from a thicker plate of 0.188 inches. It is important that the structure of laser lowering device 100 be strong, but not at the expense of making it so heavy that it could not be picked up by one person. The weight and strength elements are closely connected because they are both largely dependent on material composition. However, it will be understood by a person skilled in the art that the size, shape, materials and thickness of materials used may vary.

In an example operation, a user would first mount pipe laser 200 on to laser support 10 and secure pipe laser 200 to laser support 10 with threaded screws, or other suitable fasteners, through the non-threaded through holes (or other connecting means) and into the threaded holes (or other connecting means) of laser pipe 200. Once secured, the user would move laser lowering device 100 into the hanging position or the folded up position. The user would then insert pole 300 into pole receiving cavity 53 and begin lower laser lowering device down a riser shaft, while holding on to second line end 62. Once laser pipe 200 has reached the desired depth and/or the pit body, the user can begin pulling on mount control line 58 to retract or release mount 12 and move laser lowering device 100 into the horizontal position or any other suitably angled position for the pipe it is to be inserted into. After laser lowering device 100 has been moved into the horizontal or other angled position, the user would exert a forward pushing force on pole 300 to move pipe laser 200 into the pipe to be measured.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, functions, operations, or steps, any of these embodiments may include any modification, combination or permutation of any of the components, elements, functions, operations, or steps described or illustrated anywhere herein that a person having ordinary skill in the art would comprehend. All such modifications, combinations and permutations are believed to be within the sphere and scope of the invention as defined by the claims appended hereto.

What is claimed is:

1. A laser lowering device for mounting a laser, the laser lowering device comprising:
    at least one laser support for mounting the laser;
    a mount having a line receiving portion, the mount being connected to the at least one laser support;
    an elongated member having a first end and a second end, the first end being removably connected to a pole and the second end being pivotally connected to the mount; and
    a mount control line connected to the line receiving portion and extending towards the elongated member;
    wherein the mount control line is manipulable to cause the mount to pivot relative to the elongated member.

2. The laser lowering device of claim 1, wherein the mount is in a shape that provides for the line receiving portion to be in an offset position from a center axis of the elongated member.

3. The laser lowering device of claim 2, wherein the mount is in the shape of a triangle.

4. The laser lowering device of claim 1, wherein the elongated member comprises a protruded portion in between the first end and the second end.

5. The laser lowering device of claim 4, wherein the elongated member further comprises a rod disposed of in the protruded portion.

6. The laser lowering device of claim 5, further comprising a first sheave at the line receiving portion and a second sheave disposed of on the rod.

7. The laser lowering device of claim 6, wherein the mount control line is configured to wrap around at least a portion of each of the first sheave and the second sheave and is operable to cause the mount to pivot when manipulated.

8. The laser lowering device of claim 7, wherein the elongated member further comprises an aperture disposed of near the protruded portion.

9. The laser lowering device of claim 8, wherein the mount control line extends through the aperture and is operable to cause the mount to pivot when manipulated.

10. The laser lowering device of claim 1, wherein the at least one laser support comprises an upper support member and a lower support member.

11. The laser lowering device of claim 10, wherein the lower support member is angled inwards relative to the mount.

12. The laser lowering device of claim 11, wherein the lower support member comprises a plurality of holes for mounting the laser.

* * * * *